United States Patent
Pendleton et al.

(10) Patent No.: US 10,369,312 B2
(45) Date of Patent: Aug. 6, 2019

(54) LOW MAINTENANCE ENDOTRACHEAL TUBE DEVICE AND METHOD FOR PREVENTING VENTILATOR ASSOCIATED PNEUMONIA AND TRACHEAL ISCHEMIA

(71) Applicant: Cook Medical Technologies LLC, Bloomington, IN (US)

(72) Inventors: Steven L. Pendleton, Spencer, IN (US); Jeffrey D. Williams, Spencer, IN (US); Gary L. Neff, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 752 days.

(21) Appl. No.: 15/019,719

(22) Filed: Feb. 9, 2016

(65) Prior Publication Data
US 2016/0228662 A1    Aug. 11, 2016

Related U.S. Application Data

(60) Provisional application No. 62/114,369, filed on Feb. 10, 2015.

(51) Int. Cl.
*A61M 16/04*    (2006.01)
(52) U.S. Cl.
CPC ...... *A61M 16/044* (2013.01); *A61M 16/0438* (2014.02); *A61M 16/0443* (2014.02);
(Continued)

(58) Field of Classification Search
CPC ............ A61M 16/044; A61M 16/0438; A61M 16/0443; A61M 16/0456; A61M 16/0481;
(Continued)

(56) References Cited

U.S. PATENT DOCUMENTS 3,173,418 A    3/1965    Baran
3,481,339 A    12/1969    Puig
(Continued)

FOREIGN PATENT DOCUMENTS

DE    3509797 A1    10/1986
GB    1060629    12/1964
GB    1171439 A    11/1969

*Primary Examiner* — Gregory A Anderson
*Assistant Examiner* — Jonathan S Paciorek
(74) *Attorney, Agent, or Firm* — Brinks Gilson & Lione

(57) ABSTRACT

A method of sealing a trachea is provided that includes inserting a tracheal tube having an inflatable cuff made of a compliant material into a trachea. The method includes inflating the inflatable cuff with a fluid to a first pressure that exceeds a second pressure necessary to create a seal between the inflatable cuff and the tracheal wall. The method includes deflating the inflatable cuff by releasing a first pressure to allow the fluid to flow out of the inflatable cuff without applying vacuum pressure to the fluid while evaluating a rate of change of pressure of the fluid in the inflatable cuff. The method includes identifying a variance in the rate of change of pressure corresponding to a third pressure at which the inflatable cuff separates from the tracheal wall, determining the second pressure by analyzing the third pressure, and reinflating the inflatable cuff to the second pressure.

19 Claims, 16 Drawing Sheets

(52) U.S. Cl.
CPC .... *A61M 16/0456* (2014.02); *A61M 16/0465*
(2013.01); *A61M 16/0481* (2014.02); *A61M
2205/0222* (2013.01); *A61M 2205/3331*
(2013.01)

(58) Field of Classification Search
CPC ...... A61M 16/0465; A61M 2205/0222; A61M 2205/3331
See application file for complete search history.

(56) References Cited

U.S. PATENT DOCUMENTS

| | | | |
|---|---|---|---|
| 4,791,923 | A | 12/1988 | Shapiro |
| 4,825,862 | A * | 5/1989 | Sato ..................... A61M 16/20 137/493 |
| 5,392,774 | A | 2/1995 | Sato |
| 5,452,715 | A | 9/1995 | Boussignac |
| 6,647,984 | B1 * | 11/2003 | O'Dea ................ A61M 16/044 128/207.15 |
| 6,733,474 | B2 | 5/2004 | Kusleika |
| 7,591,830 | B2 | 9/2009 | Rutter |
| 8,307,830 | B2 | 11/2012 | Clayton |
| 2003/0041863 | A1 | 3/2003 | Hargis |
| 2003/0078538 | A1 | 4/2003 | Neale et al. |
| 2005/0284483 | A1 * | 12/2005 | Patel .................... A61M 16/04 128/207.14 |

\* cited by examiner

FIG. 4
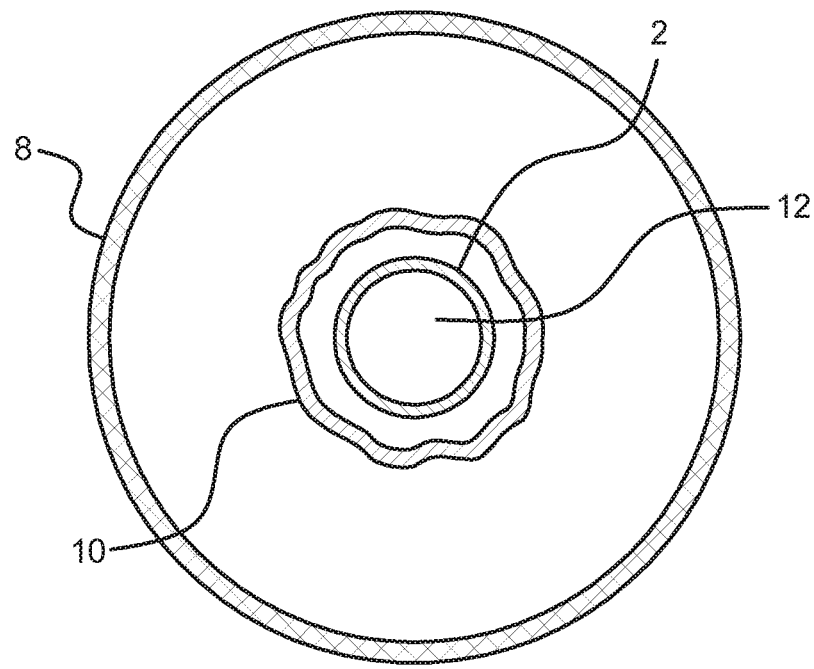
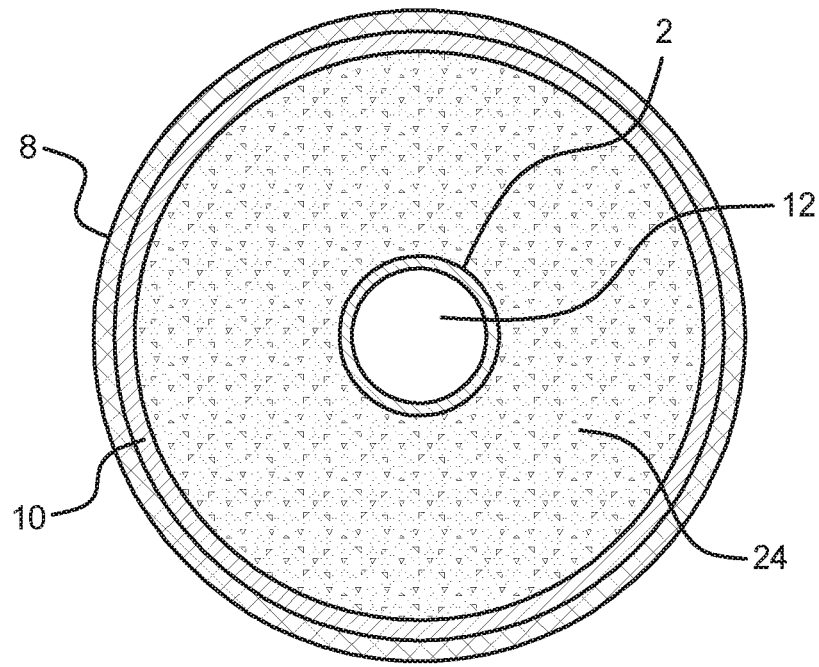

FIG. 8
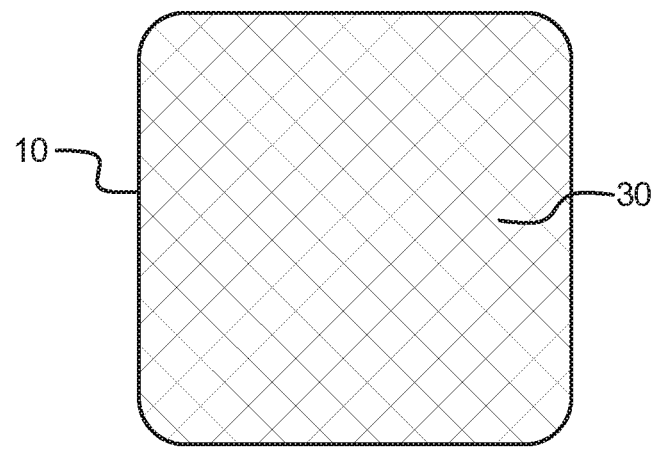
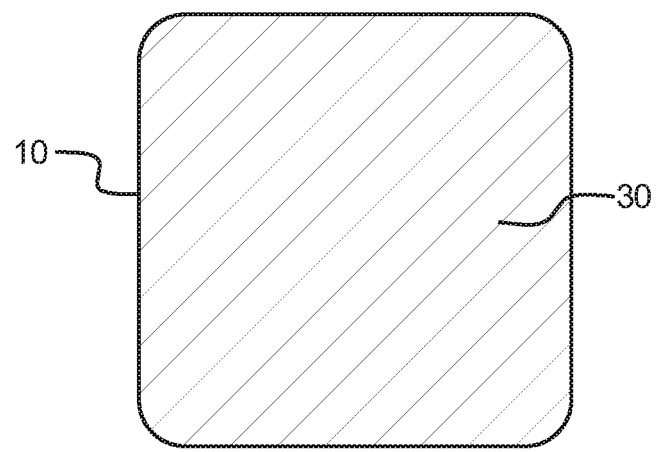
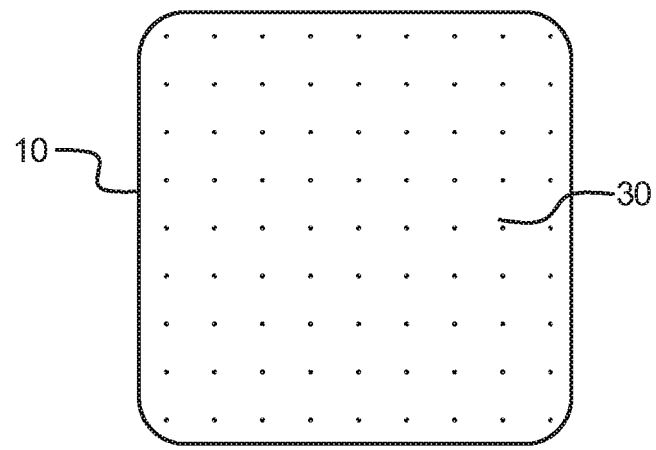

FIG. 12
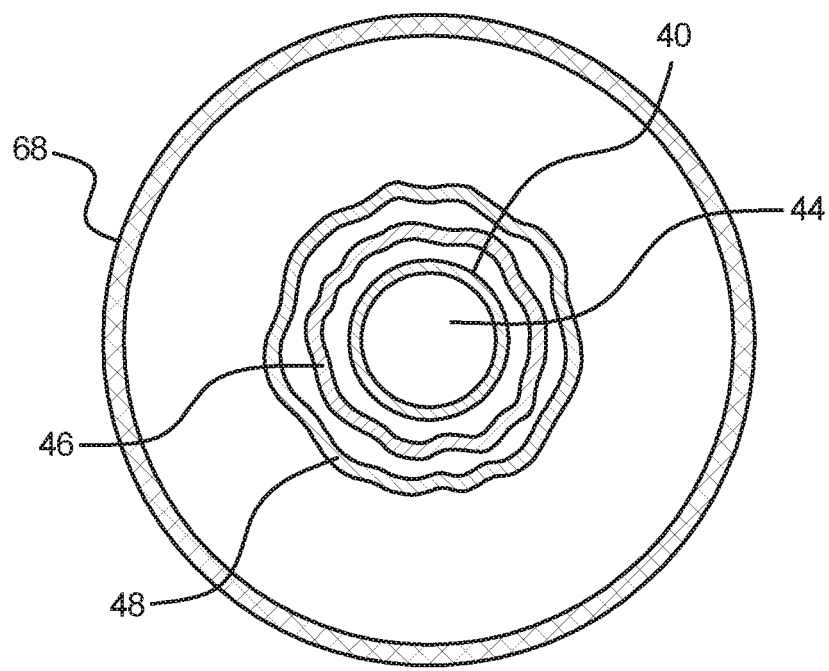
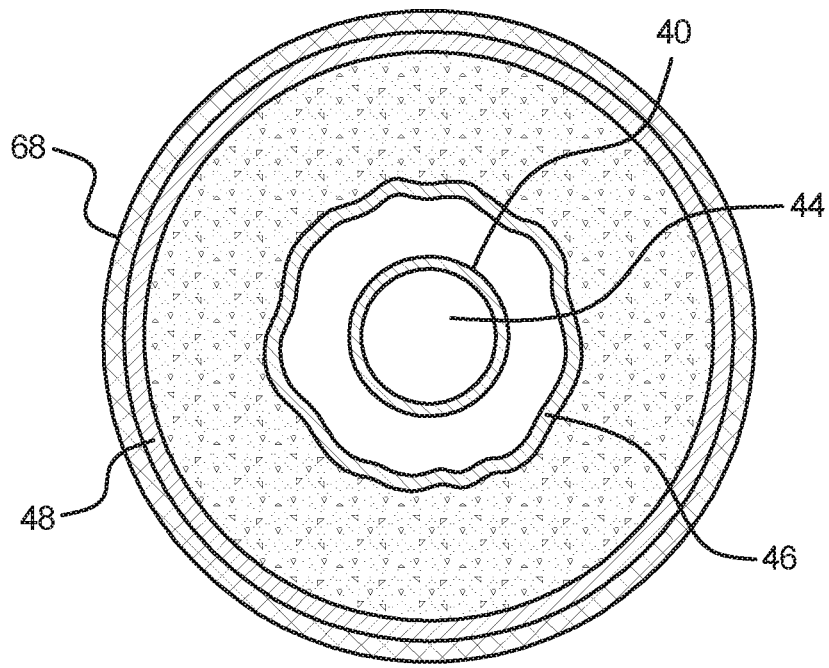

LOW MAINTENANCE ENDOTRACHEAL TUBE DEVICE AND METHOD FOR PREVENTING VENTILATOR ASSOCIATED PNEUMONIA AND TRACHEAL ISCHEMIA

CROSS-REFERENCE TO RELATED APPLICATIONS

The present patent documents claim the benefit of the filing date under 35 U.S.C. § 119(e) of Provisional U.S. Patent Application Ser. No. 62/114,369 filed Feb. 10, 2015, which is hereby incorporated by reference.

FIELD

The present disclosure relates to medical devices and more specifically to endotracheal tubes and tracheostomy tubes.

BACKGROUND

The statements in this section merely provide background information related to the present disclosure and may not constitute prior art.

Certain medical devices are used to regulate the flow of fluids and substances in and out of a patient's body. Endotracheal tubes and tracheostomy tubes are two specific examples of such a medical device. These devices, also known as tracheal tubes, assist the patient in breathing and regulate the airflow in and out of the patient's lungs. Endotracheal tubes are inserted through the patient's mouth down into the trachea, whereas tracheostomy tubes are inserted through a surgical incision in the patient's neck. Ventilators are generally attached to the tracheal tubes to assist the patient's breathing.

To ensure proper regulation of air flow and to prevent unwanted fluids or other substances from entering the lungs, a seal between the tracheal wall and the tracheal tube is desirable. With a proper seal, the only passageway into the lungs is through the regulated tracheal tube. This seal is usually achieved through the use of an inflatable cuff attached to the tracheal tube. The cuff is deflated when the device is inserted into the patient's trachea, and, once the tracheal tube is in position, the cuff is inflated to achieve a seal between the inner wall of the trachea and the outer wall of the tracheal tube. The cuffs are generally inflated with air, but other fluids can be used, including liquids. However, inflatable cuffs can cause multiple problems related to maintenance, patient discomfort, and potential medical complications. Thus, elimination of the problems related to current inflatable cuff designs is desirable.

There are two general categories of cuffs: complaint cuffs and noncompliant cuffs. Noncompliant cuffs are made of an inelastic material, typically polyvinyl chloride (PVC), and thus have a set volume when fully inflated. Noncompliant cuffs are inflated at a low pressure, which ensures that the cuff applies a corresponding low pressure against the tracheal wall when fully inflated. Therefore, patients encounter minimal discomfort when noncompliant cuffs are used. However, tracheas vary in size, ranging anywhere from 18 to 25 millimeters in diameter. To further complicate this process, clinicians do not know the diameter of the patient's trachea when performing an endotracheostomy or tracheostomy, thus they typically merely estimate the tracheal diameter based on external characteristics of the patient, such as gender and body type. Because of varying tracheal diameters, noncompliant cuffs are designed to fit any sized trachea. However, this universal cuff design presents problems, especially when a patient with a smaller trachea is presented. With the inelastic material used for noncompliant cuffs, the cuffs must have a fully inflated diameter large enough to seal the largest tracheas. Therefore, with a smaller trachea, a smooth seal is not achieved between the cuff and the tracheal wall because the cuff is not able to fully expand. Instead, cuff folds are formed due to the extra, unused material of the noncompliant cuff. These cuff folds create passageways for bacteria and other unwanted substances to travel around the tracheal tube and reach the lungs. These cuff folds can cause several complications, but the most common issue is ventilator associated pneumonia. Bacteria are able to freely colonize within these cuff folds because the cuff folds shield them from removal and treatment by clinicians. The bacteria then leaks down through the cuff folds into the lungs, causing the patient to contract pneumonia. Thus, elimination of cuff folds is a desirable goal of tracheal tube designs.

To eliminate cuff folds and their associated problems, compliant cuffs can be used. These cuffs are made of an elastic material that can be inflated to a variety of tracheal diameters while maintaining a smooth seal between the cuff and the tracheal wall. The elastic material ensures a proper seal without cuff folds regardless of the tracheal diameter. However, the elastic material is often delicate and prone to tears or leaks. Therefore, the cuff wall of a compliant cuff is usually relatively thick, which then causes the cuff to require a higher pressure to properly inflate it. Additionally, since the clinician does not know the exact size of the given trachea, the cuff is generally inflated to a pressure that ensures that the trachea will be completely sealed regardless of the actual tracheal diameter. This higher pressure, which is exacerbated in patients with smaller tracheas, causes a corresponding amount of pressure to be applied to the tracheal wall. The high pressure can cause patient discomfort and, more seriously, tracheal ischemia and even necrosis. This danger is more severe when the endotracheal or tracheostomy tube is in place for a prolonged period of time. Tracheal ischemia is a restriction in blood supply to the tissues surrounding the cuff which causes a shortage of oxygen and glucose. If ischemia persists for a long period of time, the lack of nutrition will cause necrosis to occur and the tissue will die. The risk of ischemia is greater for tracheostomy tubes, as they are generally more permanent than endotracheal tubes. Therefore, while compliant cuffs create a proper seal against the tracheal wall, elimination of the high pressure on the tracheal wall is desired.

Additionally, both compliant and noncompliant cuffs require regular maintenance to ensure proper continuous inflation. Compliant cuffs are made of highly permeable or semi-permeable materials, meaning the cuff deflates naturally at a high rate as air slowly leaks through the walls of the cuff. Thus, the pressure must be frequently checked to maintain a proper seal between the cuff and the tracheal wall. Even noncompliant cuffs, despite the use of materials with lower permeability such as PVC, still deflate eventually. Clinicians must check the cuff pressure every 4-8 hours to ensure proper continuous inflation. Often, this check is overlooked due to more critical responsibilities requiring the clinicians' attention, causing the complications discussed above to become more frequent and severe. Thus, a cuff that requires less regular maintenance is desirable.

SUMMARY

In one form of the present disclosure, a method of sealing a trachea is described. The method comprises inserting a tracheal tube that comprises an inflatable cuff into a trachea which comprises a tracheal wall. The inflatable cuff is comprised of a compliant material. The method also comprises inflating the inflatable cuff with a fluid to a first pressure that exceeds a second pressure necessary to create a seal between the inflatable cuff and the tracheal wall. The method also comprises deflating the inflatable cuff by releasing the first pressure to allow the fluid to flow out of the inflatable cuff without applying vacuum pressure to the fluid. The method also comprises evaluating a rate of change of pressure of the fluid in the inflatable cuff while the inflatable cuff is deflating. Additionally, the method includes identifying a variance in the rate of change of pressure corresponding to a third pressure at which the inflatable cuff at least partially separates from the tracheal wall. Additionally, the method comprises determining the second pressure by analyzing the third pressure and reinflating the inflatable cuff to the second pressure. In another embodiment, the steps of inflating and deflating the inflatable cuff can be repeated, wherein the third pressure is determined by analyzing a number of identified variances during the multiple deflating steps. In another embodiment, the second pressure is 0 to 50 centimeters of water more than the third pressure.

In another embodiment, the method of sealing a trachea can also define the inflatable cuff as an outer cuff and the fluid as an outer cuff fluid. The tracheal tube can also comprise an inner cuff, wherein the outer cuff surrounds the inner cuff. The method can also comprise inflating the inner cuff with an inner cuff fluid after the step of inserting a tracheal tube. Also, the step of evaluating a rate of change of pressure can comprise measuring the rate of change of pressure of the inner cuff fluid while the outer inflatable cuff is deflating, where the rate of change of pressure of the inner cuff fluid is responsive to the rate of change of pressure of the outer cuff fluid. In another embodiment, the second pressure is 0 to 50 centimeters of water more than the third pressure. Additionally, the inner cuff fluid can be comprised of a gas.

In another form of the present disclosure, a tracheal tube assembly is provided that comprises a tracheal tube with an outer surface, an air flow lumen, and an inflation lumen. The tracheal tube assembly also comprises an inflatable cuff that comprises an outer surface and a cavity, wherein the outer surface of the inflatable cuff is attached to the outer surface of the tracheal tube and the inflation lumen is connected to the cavity of the inflatable cuff. Additionally, the outer surface of the inflatable cuff comprises a muco-adhesive material.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 4 is a cross sectional view of a tracheal tube with a single inflatable cuff;

FIG. 8 is an illustration of various muco-adhesive material patterns that can be applied to an inflatable cuff;

FIG. 12 is a cross sectional view of a tracheal tube with a double inflatable cuff;

DETAILED DESCRIPTION

Figure 1:
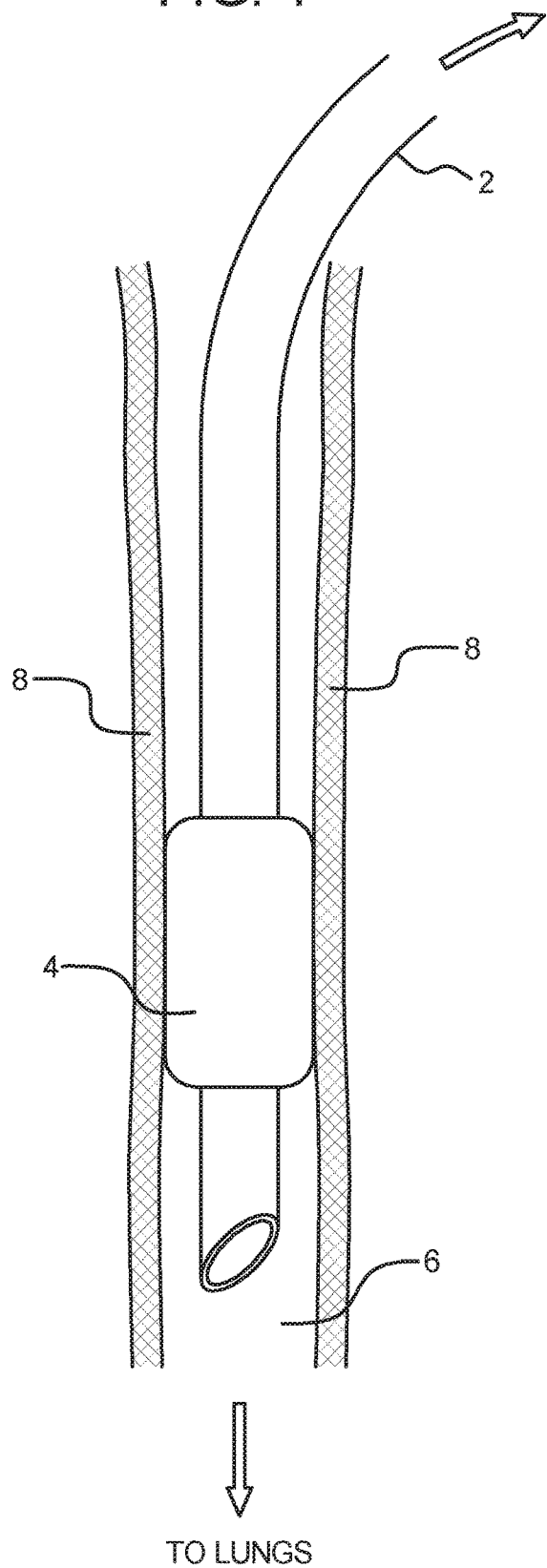
FIG. 1 is a pictorial representation of a tracheal tube and inflatable cuff constructed in accordance with the teachings of the present disclosure.

The following description is merely exemplary in nature and is not intended to limit the present disclosure, application, or uses. It should be understood that throughout the drawings, corresponding reference numerals indicate like or corresponding parts and features. It should also be understood that various cross-hatching patterns used in the drawings are not intended to limit the specific materials that may be employed with the present disclosure. The cross-hatching patterns are merely exemplary of preferable materials or are used to distinguish between adjacent or mating components illustrated within the drawings for purposes of clarity.

The present invention addresses the aforementioned shortcomings associated with tracheal tubes. This invention combines the advantages of compliant cuffs and noncompliant cuffs while limiting their respective disadvantages. The present invention reduces or eliminates cuff folds while maintaining a low pressure seal against the tracheal wall that decreases the likelihood of tracheal ischemia. Additionally, this invention reduces the amount of regular maintenance required for tracheal tubes by providing a cuff that maintains an adequate fluid pressure for an extended period of time.

While this disclosure refers only to tracheal tubes in detail, inflatable cuffs as described in this disclosure can be used in conjunction with a multitude of other medical devices that involve the sealing of an anatomical structure that is cylindrical or tubular in shape. For example, this invention may be used with esophageal, vascular, and other applications. The product or method described herein may also be used for the sizing of vessels, such as the aorta.

FIG. 1 shows a tracheal tube 2 with an inflatable cuff 4 in a patient's trachea 6. In this example, the tracheal tube 2 is an endotracheal tube, but in other embodiments the tracheal tube 2 can be a tracheostomy tube. The inflatable cuff 4 can have multiple layers, or cuffs, within the inflatable cuff 4. In this example, the inflatable cuff 4 is fully inflated to create a seal between the inflatable cuff 4 and the tracheal wall 8, thus preventing unwanted fluids and substances from leaking between the inflatable cuff 4 and the tracheal wall 8 down to the lungs.

Figure 2:
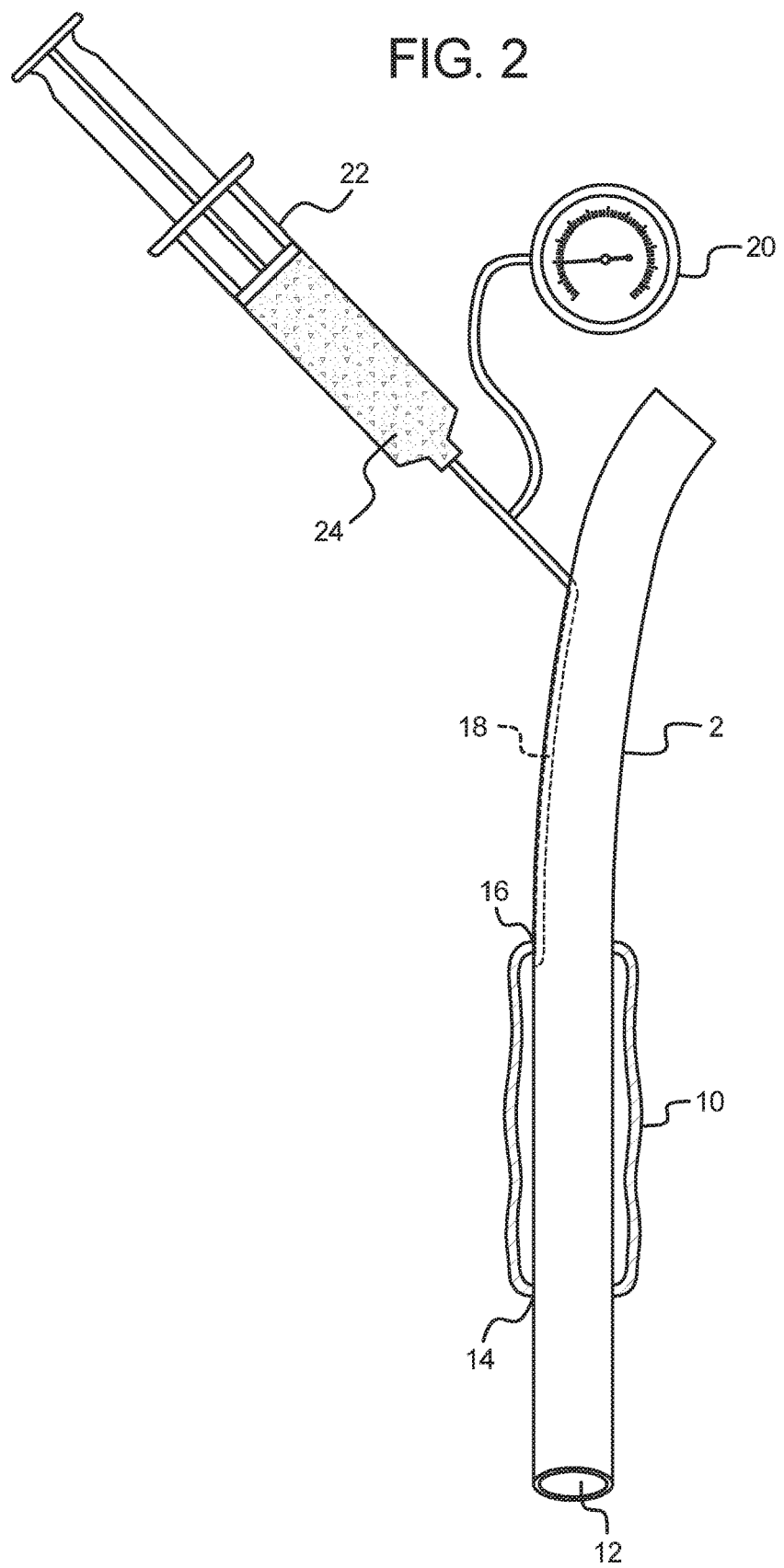
FIG. 2 is an illustration of a tracheal tube and inflatable cuff assembly with a deflated single cuff.
Figure 3:
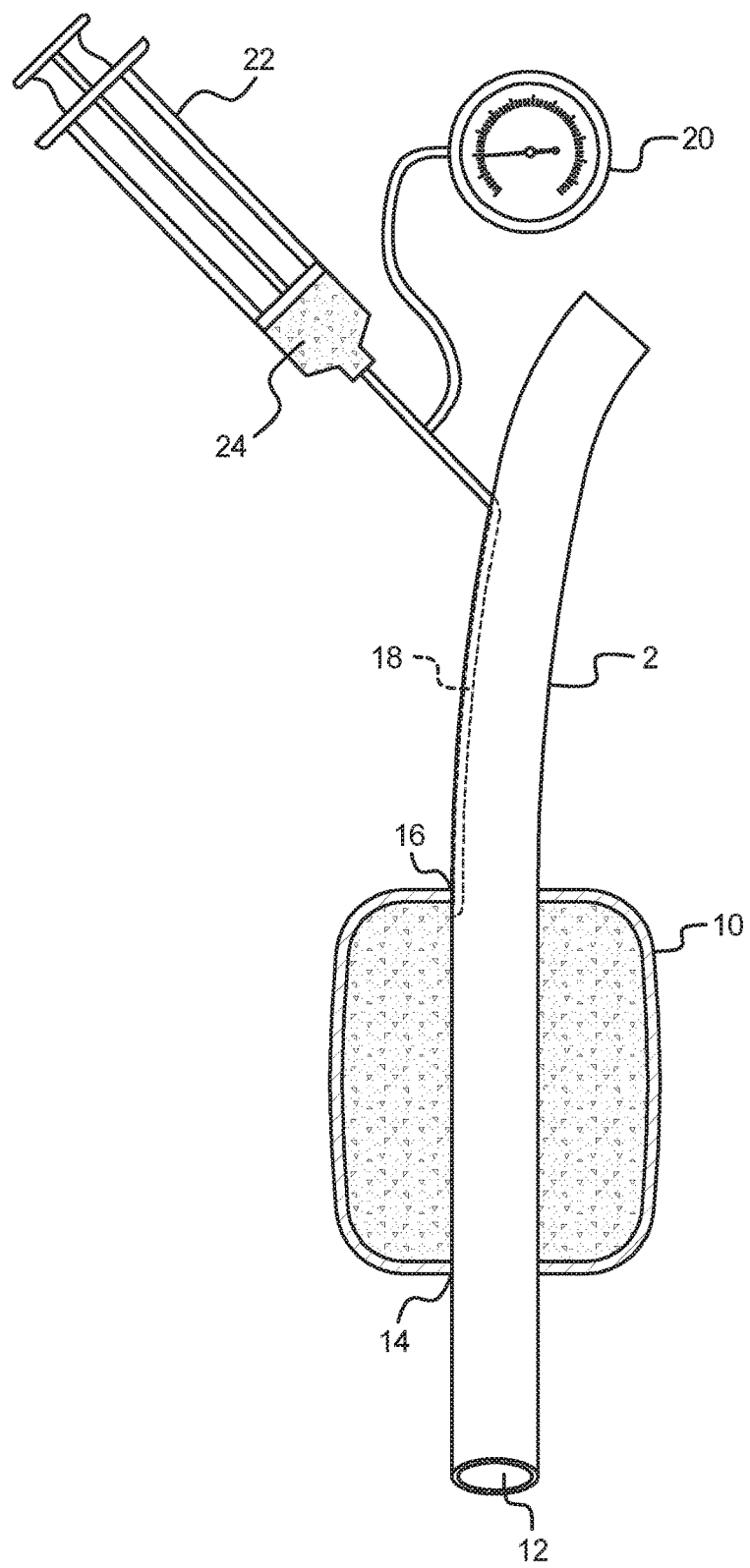
FIG. 3 is an illustration of a tracheal tube and inflatable cuff assembly with an inflated single cuff.

FIGS. 2 and 3 show one embodiment of the invention. In this embodiment, a single cuff 10 is attached to the tracheal tube 2. FIG. 2 shows the single cuff 10 in a deflated state and FIG. 3 shows the single cuff 10 in an inflated state. The tracheal tube 2 has a lumen 12 that regulates the passage of air into and out of the lungs. The single cuff 10 surrounds the tracheal tube 2 and connects to the tracheal tube 2 at two points: a distal connection point 14 and a proximal connection point 16. The single cuff 10 may be bonded to the tracheal tube 2 using an adhesive or any other type of bonding method that prevents or limits fluid leakage from the single cuff 10. The single cuff 10 is ideally made of a compliant material, preferably silicone. However, the material may also be, but is not limited to, elastomeric materials such as latex, rubber, and polyurethane. Compliance is a measure of the maximum percentage a given material can elastically expand beyond its non-stressed state while still allowing it to revert back to its non-stressed form. Compliant balloons typically have a compliance range of 20 to 500 percent; however that range can vary depending on the specific application of the balloon. In some cases, the compliance can be greater than 500 percent.

Still referring to FIGS. 2 and 3, the single cuff 10 may be inflated and deflated with a fluid 24 using an inflation lumen 18. The inflation lumen 18 may extend from the single cuff 10 to a point external from the patient where a clinician may easily access it. In this embodiment, the fluid 24 is a liquid, ideally saline or water. A liquid is preferred because of the slower rate at which a liquid would permeate through the wall of the single cuff 10. A liquid filled single cuff 10 will maintain an adequate pressure for a longer period of time than if the single cuff 10 was filled with gas. However, other liquids or fluids, including gases, may be used as long as the fluid 24 is sterile. The fluid pressure of the single cuff 10 is measured using a pressure measurement device 20, such as a pressure gauge or meter. A flow meter can also be used that detects the rate of flow of the fluid 24 in and out of the single cuff 10. The single cuff 10 may be inflated or deflated with a syringe 22 filled with the fluid 24 and connected to the inflation lumen 18.

FIG. 4 shows a cross section view of the single cuff 10 within the trachea 8 while the single cuff 10 is inflated and deflated. As can be seen, because the single cuff 10 is made of a compliant material, when it is inflated with the fluid 24, a smooth seal is made between the tracheal wall 8 and the single cuff 10. Thus, unwanted substances or fluids are prevented from traveling around the single cuff 10 and down towards the lungs.

Figure 5:
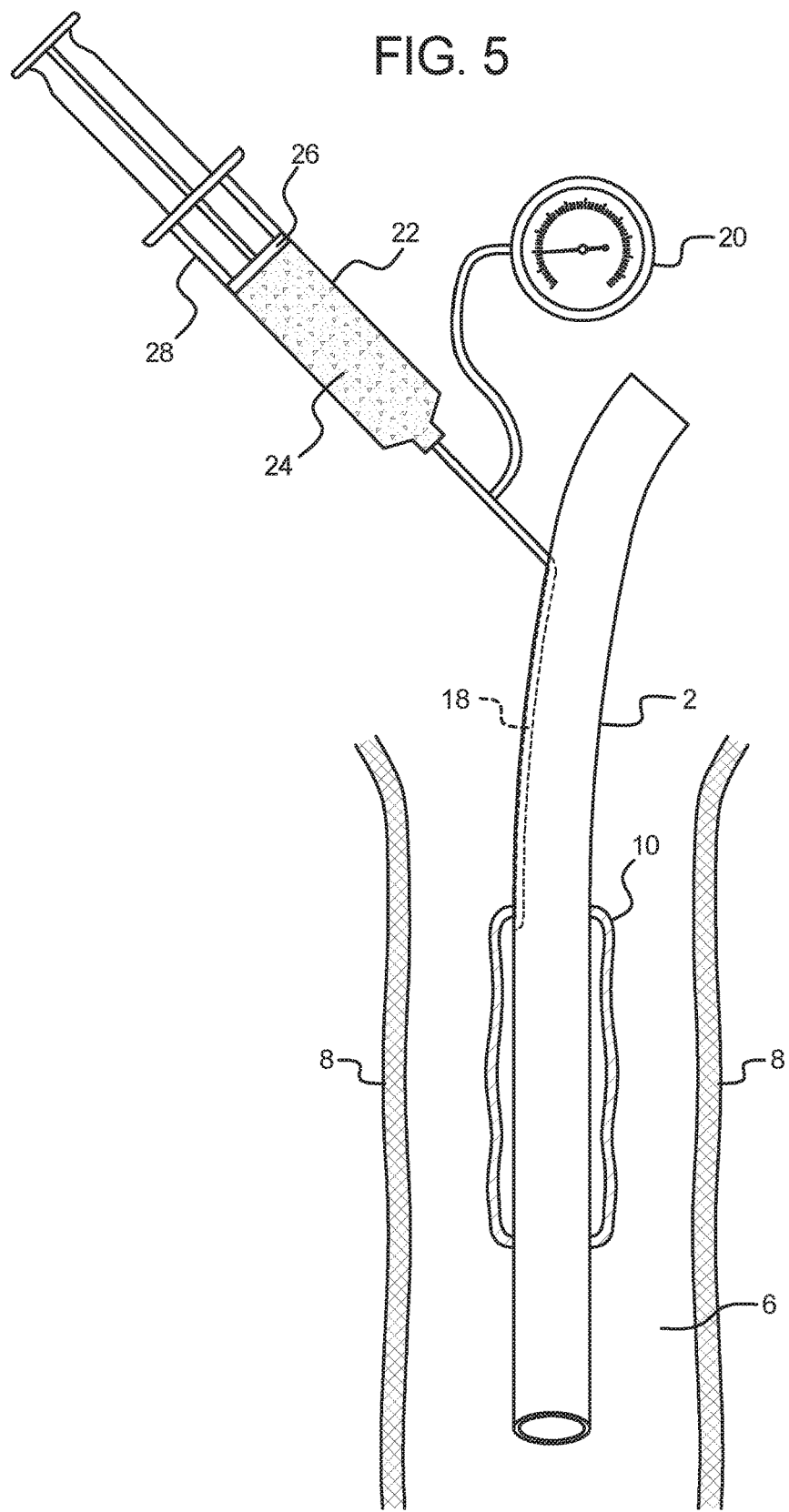
FIG. 5 is a pictorial representation of a step of inflating a single cuff.
Figure 6:
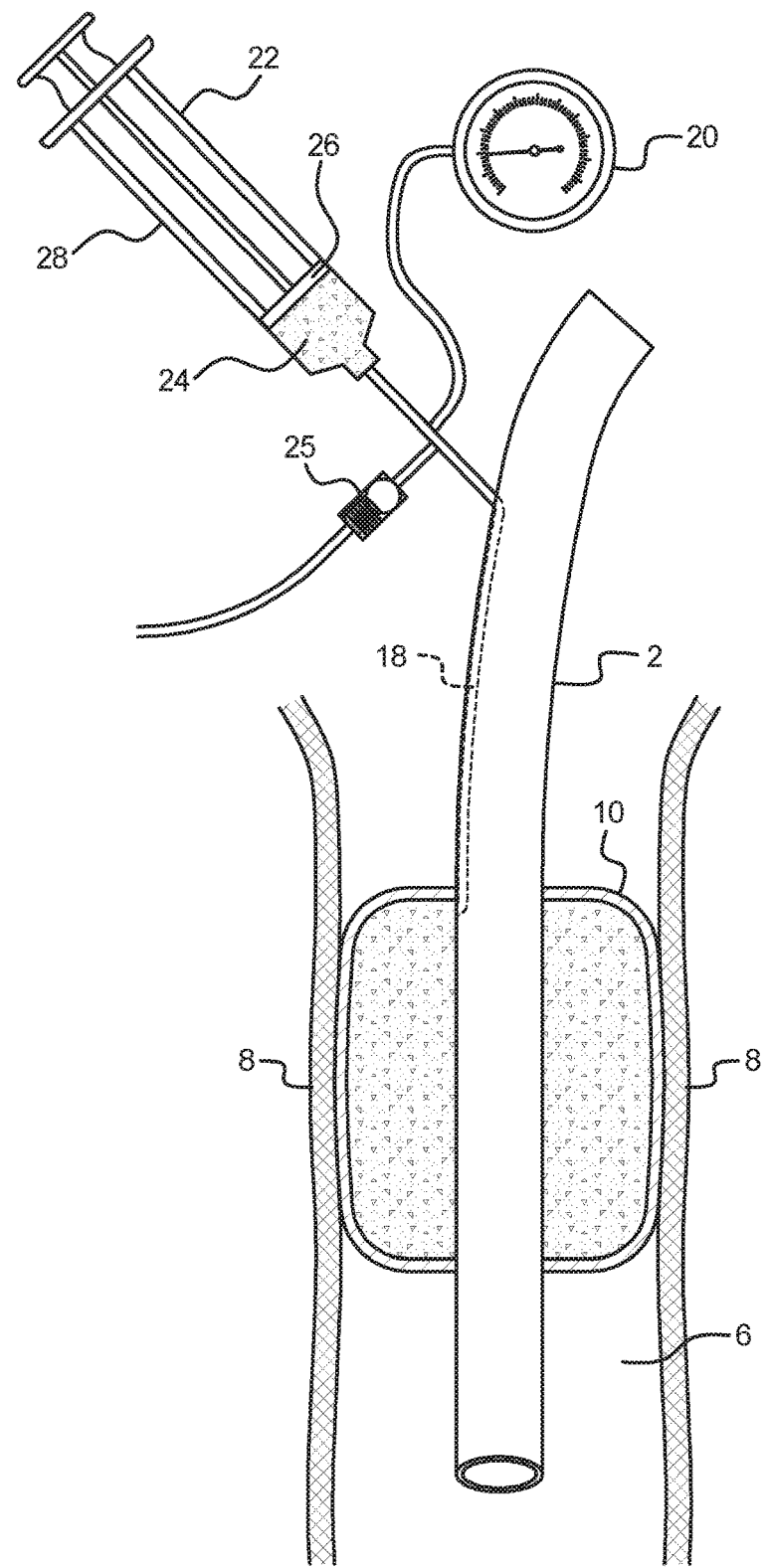
FIG. 6 is another pictorial representation of a step of inflating a single cuff.
Figure 7:
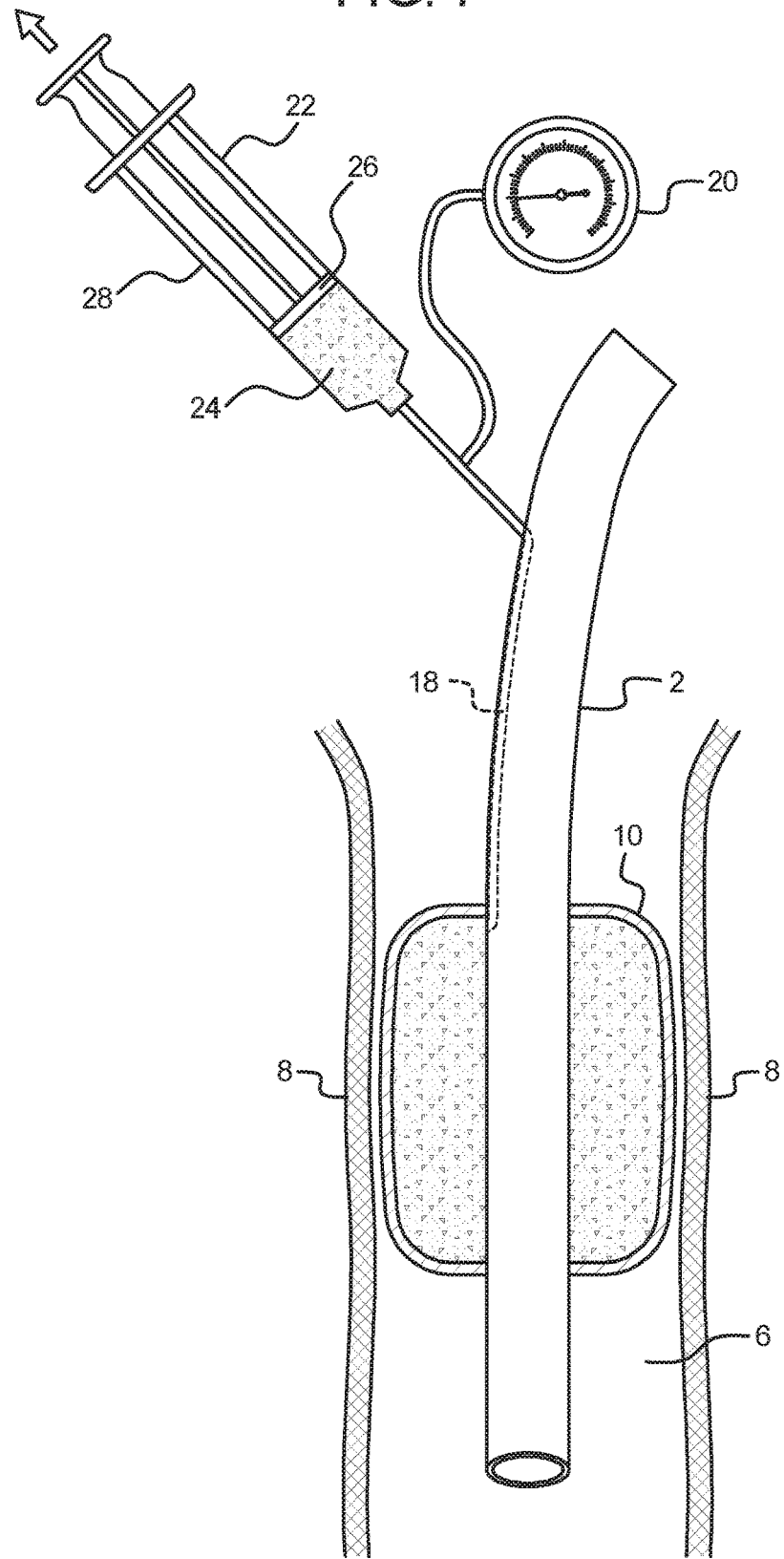
FIG. 7 is another pictorial representation of a step of inflating a single cuff.

In this embodiment, the single cuff 10 is preferably inflated in a particular way to ensure a proper seal between the single cuff 10 and the tracheal wall 8. FIGS. 5, 6, and 7 show the steps of this process. First, referring to FIG. 5, the tracheal tube 2, with the single cuff 10 deflated, is inserted into the trachea 6 through the patient's mouth. Once the tracheal tube 2 is in position, the single cuff 10 is inflated via the inflation lumen 18 with the syringe 22. The single cuff 10 is inflated with a fluid 24, ideally a liquid. As the single cuff 10 is inflated, the fluid pressure of the single cuff 10 is continuously monitored using a pressure measurement device 20.

Now referring to FIG. 6, the single cuff 10 is inflated to a pressure greater than the pressure necessary to create a seal between the single cuff 10 and the tracheal wall 8. The pressure necessary to create a seal is unknown at this point since the tracheal diameter is unknown, so the single cuff 10 is overinflated to a pressure high enough to create a seal for even the largest tracheas. This pressure varies based on the material used for the cuff and the corresponding elasticity of the material. Once the single cuff 10 is overinflated, the single cuff 10 is deflated by releasing the pressure applied to the single cuff 10 to allow the fluid 24 to flow out of the single cuff 10. Ideally, the pressure is released by removing the force initially applied to the syringe 22 inflate the single cuff 10 and allowing the fluid 24 to flow back into the syringe 22. Alternatively, the pressure can be released by opening a valve 25 attached to the inflation lumen 18 and allowing the fluid 24 to flow through the valve 25. Due to the high pressure in the single cuff 10, the fluid 24 will naturally flow back into the syringe 22 or through the valve 25, thereby gradually deflating the single cuff 10.

When deflating the single cuff 10 by allowing the fluid 24 to flow back into the syringe 22, the single cuff 10 will ideally deflate at a steady rate. To ensure a steady rate, the sliding friction between the syringe 22 and the plunger 26 must be low. If the sliding friction is too high, the fluid 24 will not naturally flow back into the syringe 22. To reduce the sliding friction, the syringe 22 is ideally a glass or plastic syringe with a rubber plunger 26. In another potential embodiment, the syringe 22 is made of glass with a fitted tungsten or stainless steel plunger 26. Additionally, the plunger 26 may be coated with a fluoropolymer, silicone oil, mineral oil, or some other lubricant to reduce the sliding friction between the plunger 26 and the wall 28 of the syringe 22.

Now referring to FIG. 7, as the single cuff 10 is deflating, the pressure of the fluid 24 in the single cuff 10 is continuously monitored using the pressure measurement device 20. The fluid pressure will steadily drop as the single cuff 10 deflates. Eventually, the single cuff 10 will begin to separate from the tracheal wall 8. As this separation begins, the single cuff 10 will tend to resist separating from the tracheal wall 8 because the single cuff 10 has adhered to the tracheal wall 8. However, as the single cuff 10 continues to deflate, the elastic material of the single cuff 10 will naturally tend to contract to its non-expanded form. Thus, the single cuff 10 will eventually separate from the tracheal wall 8. At this separation point, the pressure of the single cuff 10, as measured by the pressure measurement device 20, may increase suddenly due to the elastic material of the single cuff 10 suddenly separating from the tracheal wall and returning to its non-expanded state. This sudden contraction causes a sudden decrease in the volume of the single cuff 10 and a corresponding increase in pressure. Alternatively, rather than increasing suddenly, the pressure of the single cuff 10 may remain constant for a short period of time at the separation point. While to this point the rate of change in pressure of the fluid 24 remains relatively constant during the deflation of the single cuff 10, the separation point represents a variance in the rate of change of the fluid pressure. After the separation point, the single cuff 10 will resume deflating at a relatively constant rate, albeit at a slower rate than before the separation point due to the lower pressure of the fluid 24 after separation. The difference in the rate of change of pressure in the single cuff 10 before and after the separation point provide an additional, measurable variance in the rate of change of the pressure of the fluid 24. Due to this variance, the separation point can be found and the pressure of the fluid 24 at the separation point is recorded. For increased accuracy, the single cuff 10 can be inflated and deflated multiple times to find the separation point and the corresponding fluid pressure in the single cuff 10. The separation point corresponds to the point at which the single cuff 10 is applying zero pressure to the tracheal wall 8, but still contacting it.

Based on the separation point and the corresponding pressure of the fluid 24 in the single cuff 10, the clinician can determine to what pressure to inflate the single cuff 10. To achieve a seal between the tracheal wall 8 and the single cuff 10, the single cuff 10 should be inflated, at a minimum, to the pressure of the fluid 24 at the separation point. However, to ensure that there is a proper seal the single cuff 10 is ideally inflated to a point where the pressure of the fluid 24 is 5 to 50 cm $H_2O$ greater than the pressure at the separation point, although that range can be adjusted. To prevent patient discomfort and tracheal ischemia, the single cuff 10 should not be inflated to a pressure much greater than the given range. Since clinicians do not know the tracheal diameter of any given patient, the separation point allows clinicians to accurately determine the pressure needed to create a proper seal for each individual patient. Therefore, this process lessens the risk of over pressurizing the single cuff 10 and causing patient discomfort and ischemia. Additionally, this process ensures a proper seal between the single cuff 10 and the tracheal wall 8.

For there to be a measurable separation point and a corresponding pressure jump or pressure pause of the fluid 24, the single cuff 10 is ideally made of a material that adheres to the tracheal wall 8. While silicone, the material used for the single cuff 10 in the present embodiment, will adhere at least partially to the tracheal wall 8, another material can be used to increase the adherence and thereby enhance the visibility of the separation point. To achieve adherence, materials with muco-adhesive properties may be used. Muco-adhesiveness is a measure of the ability of a material to adhere to a mucosal layer. The mucosal layer, a viscoelastic fluid made primarily of mucus, lines the exposed surfaces of internal organs, such as the tracheal wall 8. Thus, using muco-adhesive materials with the single cuff 10 will cause the single cuff 10 to adhere to the tracheal wall 8. As the muco-adhesiveness of the outer layer of the single cuff 10 increases, the single cuff's 10 adherence to the tracheal wall 8 increases. Correspondingly, the pressure jump of the fluid 24 will be more visible to the operator. Examples of muco-adhesive materials that can be used to enhance the visibility of the separation point include, but are not limited to, anionic polymers such as polyacrylic acid, polymethacrylic acid, carboxymethylcellulose, sodium aliginate, poly[(maleic acid)-co-(vinyl methyl ether)], carbomer, and carbopol polymers. Additionally, cationic polymers such as chitosan and polymethacrylates, amphoteric polymers such as gelatin and N-carboxymethylchitosan, and polymeric thiomers such as conjugates of poly (acrylic acid)/cysteine, chitosan/N-acetylcysteine, alginate/cysteine, chitosan/thioglycolic acid, and chitosan/thioethylamidine may be used. Additional materials that may be used include amylose, amylopectin, fibrin glue, porcine small intestinal submucosa, and hydroxypropyl methyl cellulose.

However, most of the muco-adhesive materials discussed above are noncompliant or semi-compliant, making them unideal materials for the single cuff 10, as a compliant material is preferred. Thus, rather than using the muco-adhesive materials for the single cuff 10, a muco-adhesive layer 30 may be bonded to the compliant single cuff 10 using various patterns or markings as shown in FIG. 8. Potential patterns used for the muco-adhesive layer 30 can include, but are not limited to, dots, various hatches, and lines. In this situation, the single cuff 10 is still primarily made of silicone or some other compliant material, while the muco-adhesive layer 30 has a pattern that enhances the visibility of the separation point without compromising the compliancy of the single cuff 10. Alternatively, the muco-adhesive layer 30 may be applied to the compliant single cuff 10 in a solid layer that is thin enough to allow unimpeded cuff expansion upon inflation while allowing adequate cuff compliance to occur. The acceptable thickness of a solid muco-adhesive layer 30 depends on the muco-adhesive material used as well as the material used for the single cuff 10. Additionally, while the muco-adhesive layer 30 may adhere to the tracheal wall 8, the muco-adhesive layer 30 may not properly bond to the single cuff 10 because of material incompatibilities. Therefore, a tye, or intermediate, layer may be used between the single cuff 10 and the muco-adhesive layer 30 to ensure all layers are properly bonded together.

Figure 9:
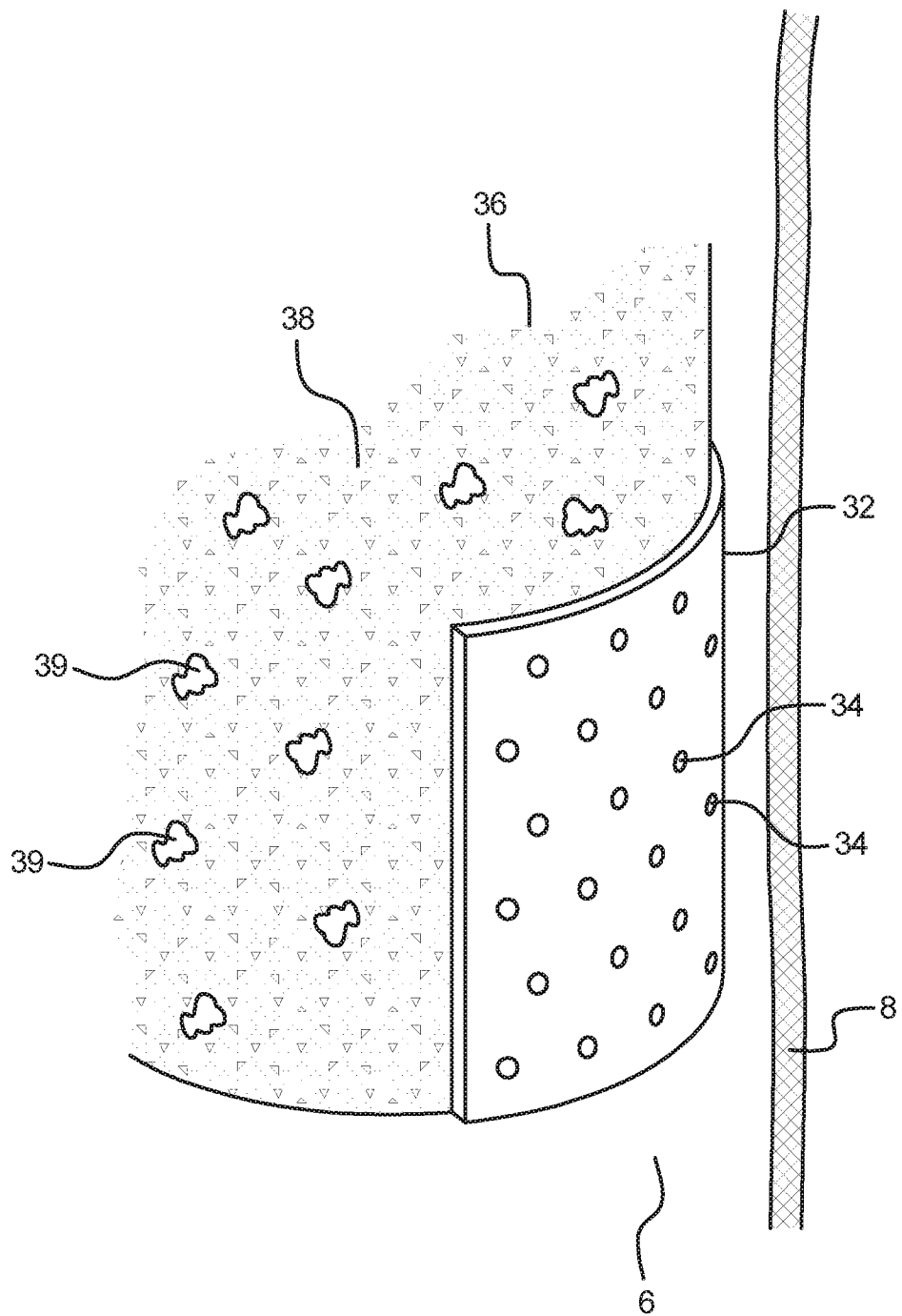
FIG. 9 is an illustration of a porous cuff filled with an aqueous-jelly solution.

In another embodiment of the invention, a porous cuff 32 made of a compliant material is provided as shown in FIG. 9. The porous cuff 32 has pores 34 that allow the weeping of a fluid through the porous cuff 32. Ideally, the cuff will have a porosity between 0.00001% and 0.5%, which refers to the percentage of the porous cuff 10 that is open air. The porosity is ideally high enough to allow a fluid to weep through the porous cuff 32, but not so high that the porous cuff 32 deflates at an undesirable rate. The porous cuff 32 may be inflated with an aqueous-jelly solution 36. This aqueous-jelly solution 36 can be made of two parts: a liquid 38 and a water soluble lubricating jelly 39. The liquid 38 must be sterile, preferably saline or water. The water soluble lubricating jelly 39 is a sterile, gelatinous substance that can be dissolved in an aqueous solution. The water soluble lubricating jelly 39 can be made of, but is not limited to, glycerol, carboxymethyl cellulose, hypromellose, and propylene glycol.

The ratio of the liquid 38 to the water soluble lubricating jelly 39 preferably ranges from 75% liquid 38 and 25% water soluble lubricating jelly 39 to 25% liquid 38 and 75% water soluble lubricating jelly 39. When the porous cuff 32 is filled with the aqueous-jelly solution 36, the aqueous-jelly solution 36 will weep through the pores 34 in the porous cuff 32 into the trachea 6. Once in the trachea 6, the water soluble lubricating jelly 39 acts as an adhesive or bonding agent that fills any existing gaps between the tracheal wall 8 and the porous cuff 32. The aqueous-jelly solution 36 may also be used to fill the single cuff 10 of the previous embodiment. The mixture may help lessen the rate at which the fluid 24 would permeate through the single cuff 10.

Figure 10:
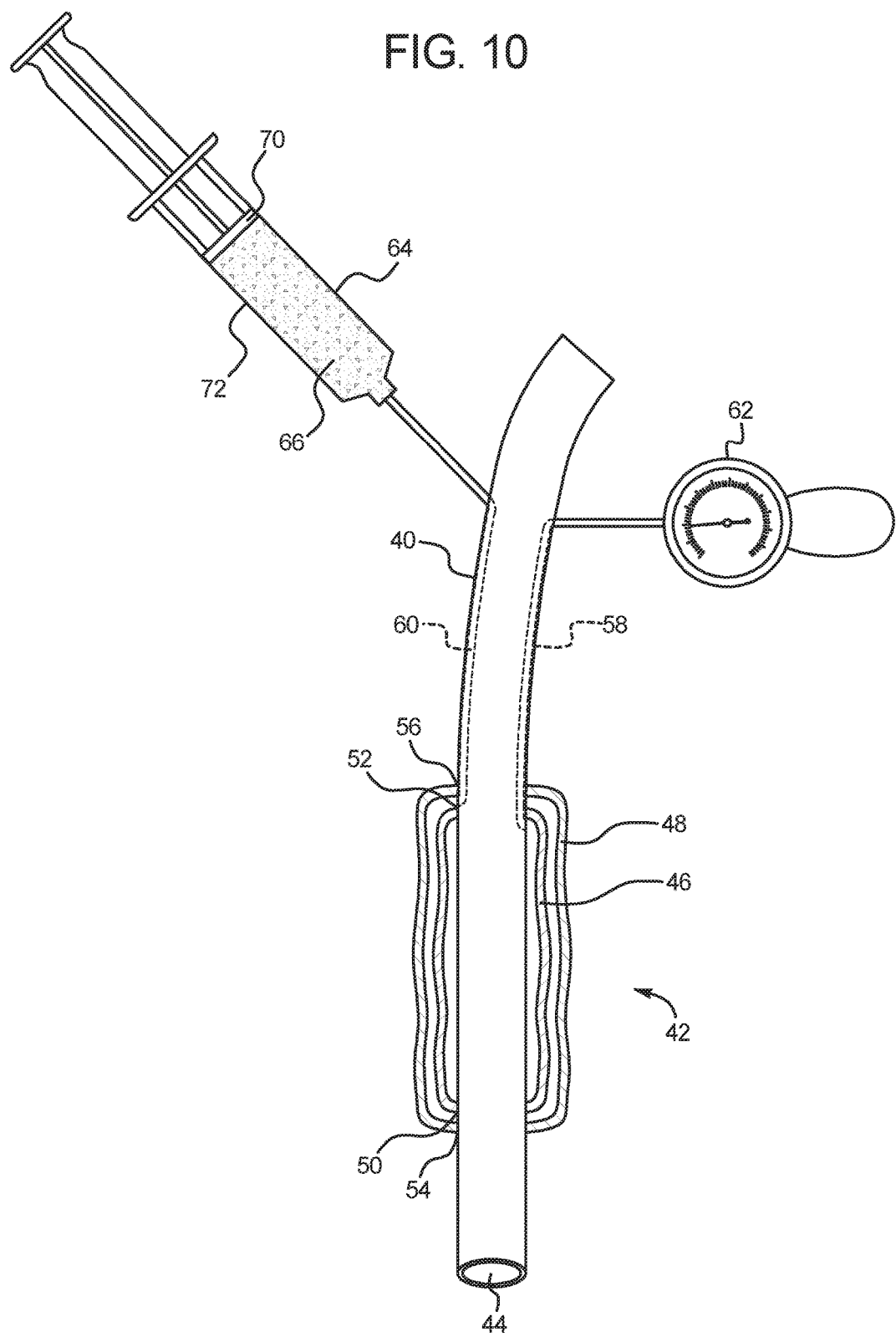
FIG. 10 is an illustration of a tracheal tube and inflatable cuff assembly with a deflated double cuff.
Figure 11:
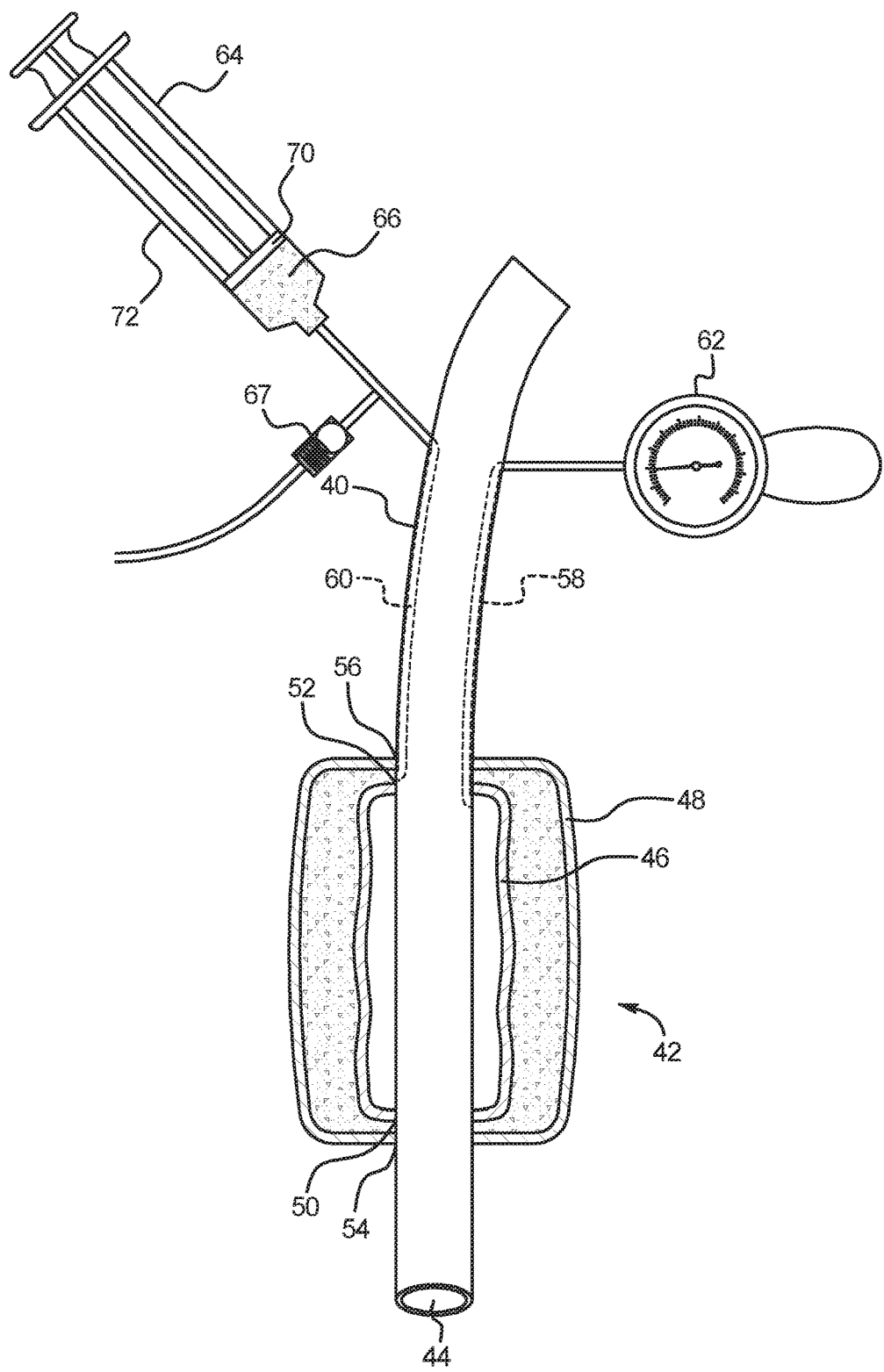
FIG. 11 is an illustration of a tracheal tube and inflatable cuff assembly with an inflated double cuff.

Another embodiment of the invention is shown in FIGS. 10 and 11. In this embodiment, a tracheal tube 40 with an inflatable cuff 42 is shown. FIG. 10 shows the inflatable cuff 42 in a deflated state, while FIG. 11 shows the inflatable cuff 42 fully inflated. The tracheal tube 40 has a lumen 44 that regulates the passage of air into and out of the lungs. The inflatable cuff 42 surrounds the tracheal tube 40 and has two layers: an inner cuff 46 and an outer cuff 48. The inner cuff 46 is ideally made of a noncompliant or semi-compliant material, such as nylon, polyvinyl chloride (PVC), polyethylene, or polyethylene terephthalate. Noncompliant balloons typically have a compliance range of 0 to 10 percent. Semi-compliant balloons typically have a compliance range of 5 to 30 percent. However these ranges may vary depending on the specific application of each balloon. The outer cuff 48 is ideally made of a compliant material, such as silicone, latex, rubber, or polyurethane. As discussed above, compliant balloons typically have a compliance of 20 to 500 percent; however this range may vary. The inner cuff 46 and outer cuff 48 are bonded to the tracheal tube 40 using an adhesive or any other type of bonding method that prevents or limits fluid leakage from the inflatable cuff 42. The inner cuff 46 has two connection points to the tracheal tube 40: a distal inner cuff connection point 50 and a proximal inner cuff connection point 52. The outer cuff 48 has two connection points to the tracheal tube 40: a distal outer cuff connection point 54 and a proximal outer cuff connection point 56. Ideally, the distal outer cuff connection point 54 is more distal than the distal inner cuff connection point 50 and the proximal outer cuff connection point 56 is more proximal than the proximal inner cuff connection point 52 so that the outer cuff 48 completely surrounds the inner cuff 46.

Still referring to FIGS. 10 and 11, the inner cuff 46 may be inflated and deflated using an inner inflation lumen 58, and the outer cuff 48 may be inflated and deflated using an outer inflation lumen 60. The inner inflation lumen 58 and outer inflation lumen 60 may extend from their respective cuffs to a point external from the patient where the clinician may easily access them to inflate and deflate the cuffs.

In this embodiment, the inner cuff 46 is inflated with a fluid via the inner inflation lumen 58 using a manometer 62. Air or some other gas is preferable over a liquid because gasses are more responsive to slight changes in pressure, meaning any variance in pressure will be more easily detected than if a liquid is used; however, liquids may be used. The manometer 62 has the dual function of inflating the inner cuff 46 and measuring the air pressure of the inner cuff 46. However, other pressure measurement and inflation devices may be used. The outer cuff 48 is inflated with a fluid 66. While the fluid 66 is ideally a liquid, such as water or saline, gases may be used. The outer cuff 48 may be inflated via the outer inflation lumen 60 with the use of a syringe 64 filled with the fluid 66.

FIG. 12 shows a cross sectional view of the inflatable cuff 42 with the inflatable cuff 42 both inflated and deflated. As can be seen, when the outer cuff 48 is fully inflated, a proper seal between the outer cuff 48 and the tracheal wall 68 is achieved because the outer cuff 48 is made of a compliant material. Additionally, the inner cuff 46, made of a noncompliant or semi-compliant material, may still have cuff folds when the inflatable cuff 42 is inflated, but the cuff folds have no effect on the seal between the outer cuff 48 and the tracheal wall 68. Since there are no cuff folds on the outer cuff 48, passageways for bacteria and other unwanted substances are eliminated.

Figure 13:
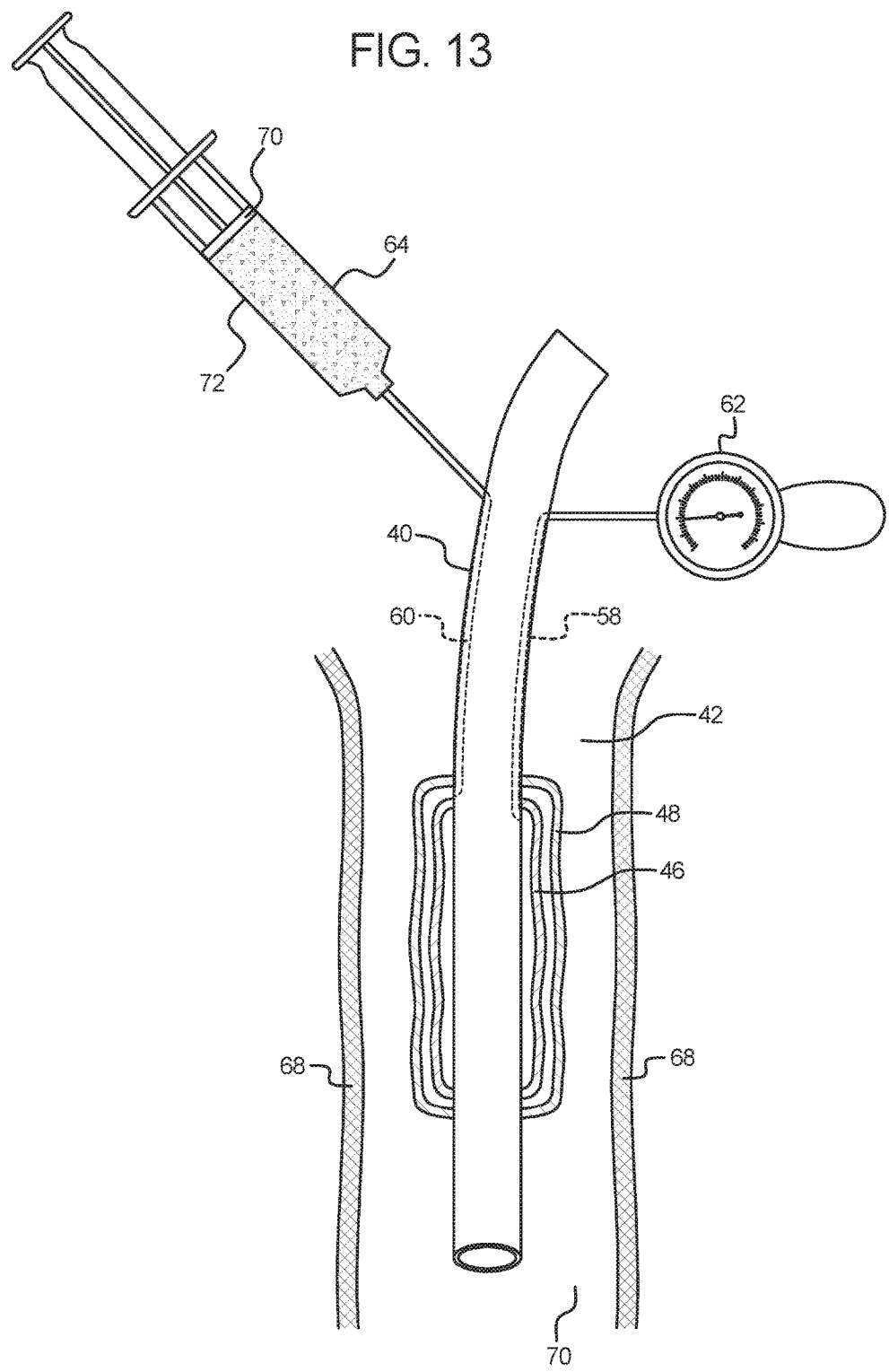
FIG. 13 is a pictorial representation of a step of inflating a double cuff.

To ensure that a proper seal is created between the inflatable cuff 42 and tracheal wall 68, the inflatable cuff 42 must be inflated in a particular way. FIGS. 13-16 show this process in detail. Referring to FIG. 13, the tracheal tube 40 is first inserted into the trachea 70 through the patient's mouth. During this step, both the outer cuff 48 and the inner cuff 46 are deflated.

Figure 14:
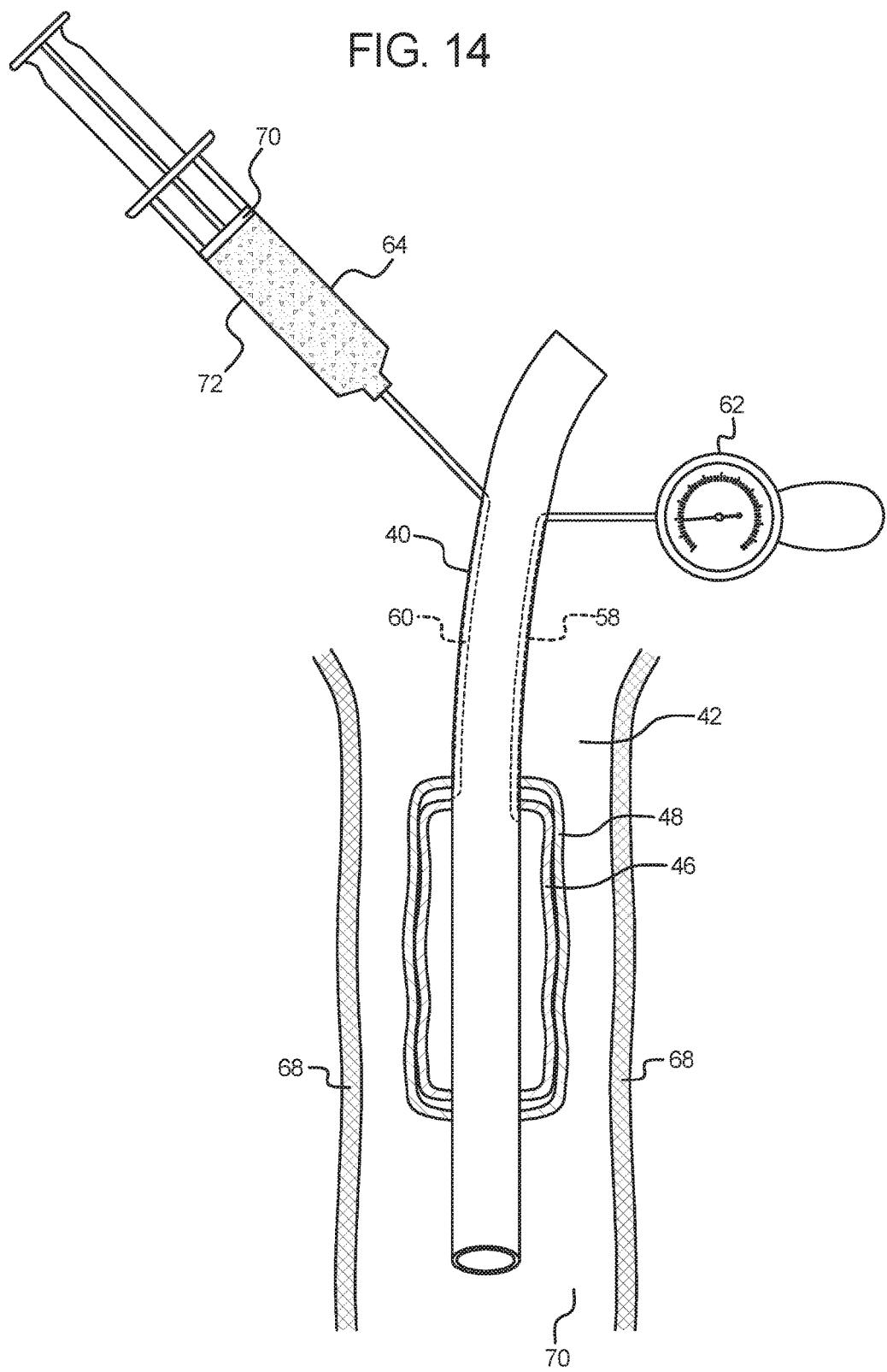
FIG. 14 is another pictorial representation of a step of inflating a double cuff.

Now referring to FIG. 14, the inner cuff 46 is over-inflated via the inner inflation lumen 58 with air using a manometer 62 to a pressure of over 80 cm $H_2O$. While the over-inflation step is not critical to the process, it ensures that any folds or air pockets in the deflated inner cuff 46 will not cause inaccuracies in future pressure measurements. The inner cuff 46 is then deflated to a low pressure, ideally between 20 and 32 cm $H_2O$.

Figure 15:
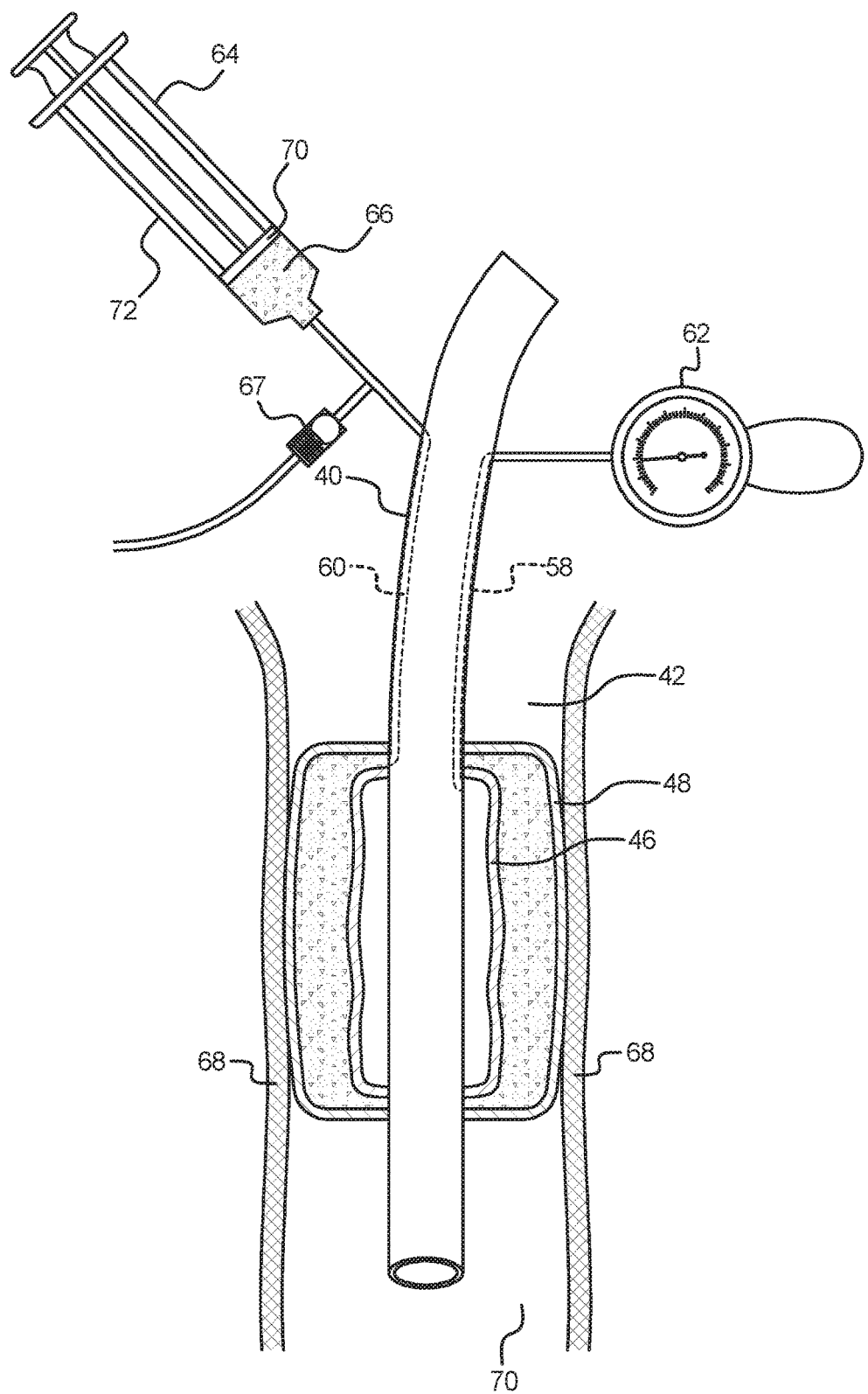
FIG. 15 is another pictorial representation of a step of inflating a double cuff.

Referring to FIG. 15, the outer cuff 48 is then inflated via the outer inflation lumen 60 with a fluid 66, ideally a liquid. In this embodiment, the fluid 66 is a saline solution; however, other liquids such as water or any other sterile liquid may be used. Using a liquid rather than a gas to inflate the outer cuff 48 ensures that the inflatable cuff 42 will stay inflated for a longer period of time because a liquid will not permeate through the outer cuff 48 as quickly as a gas. The fluid 66 can be placed within a syringe 64 and may then be injected into the outer cuff 48 through the outer inflation lumen 60. While the outer cuff 48 is being inflated, the air pressure of the inner cuff 46 may be continuously monitored using the manometer 62. The outer cuff 48 is inflated to a pressure greater than the pressure necessary to create a seal between the inflatable cuff 42 and the tracheal wall 68. Since this pressure is unknown, the outer cuff 48 is overinflated as indicated by the pressure change in the inner cuff 46. As the outer cuff 48 is inflated, the increased pressure against the inner cuff 46 by the outer cuff 48 causes the pressure in the inner cuff 46 to increase. The outer cuff 48 is ideally inflated to a point where the pressure in the inner cuff 46 is over 100 cm $H_2O$, although that range can be adjusted based on factors such as the materials and fluids used.

Figure 16:
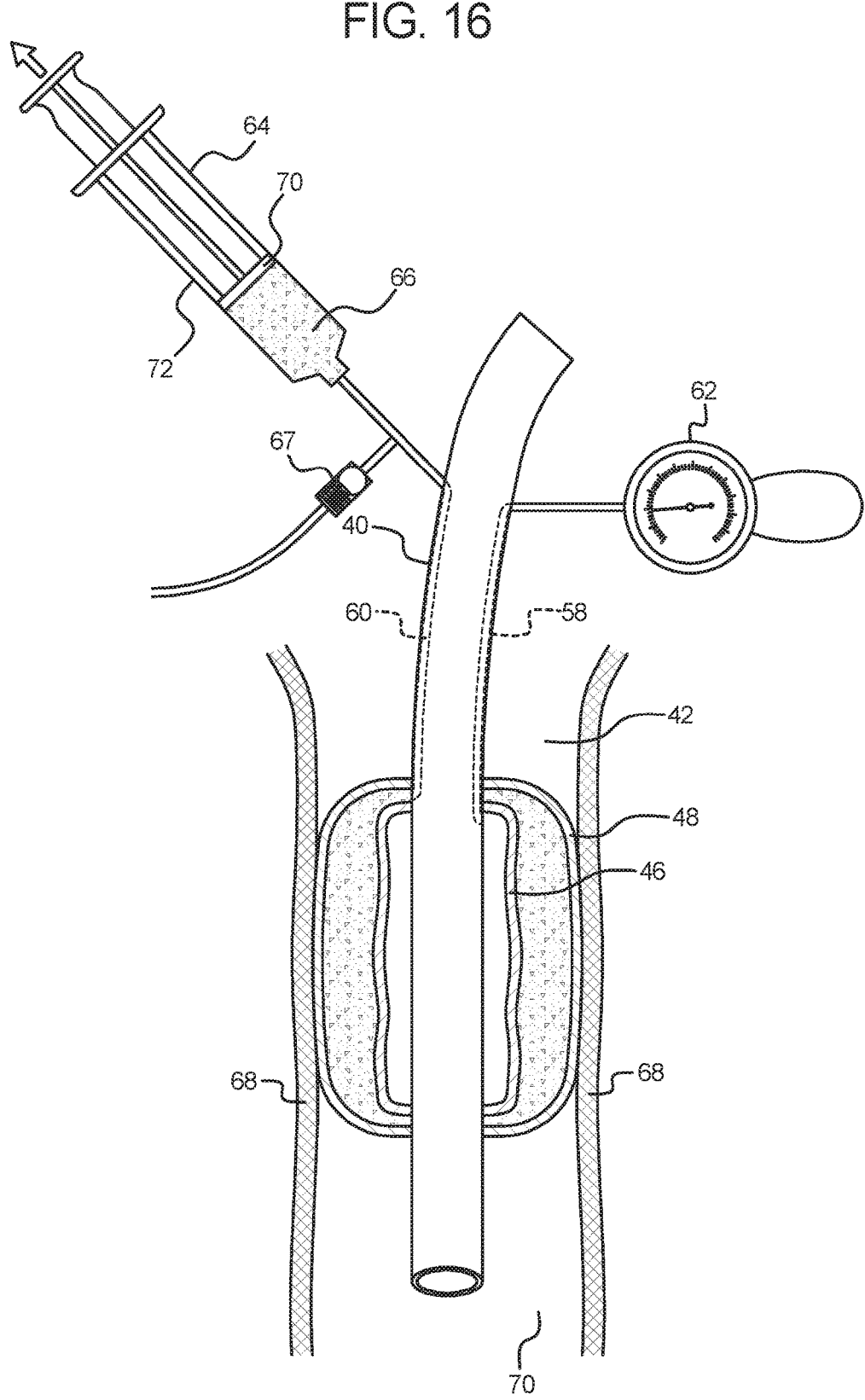
FIG. 16 is another pictorial representation of a step of inflating a double cuff.

Now referring to FIGS. 15 and 16, once the outer cuff 48 is overinflated, the outer cuff 48 is then deflated by releasing the pressure applied to the outer cuff 48 to allow the fluid 66 to flow out of the outer cuff 48. Ideally, the pressure is released by removing the force initially applied to the syringe 64 to inflate the outer cuff 48 and allowing the fluid 66 to flow back into the syringe 64. Alternatively, the pressure can be released by opening a valve 67 attached to the outer inflation lumen 60. Due to the high pressure in the outer cuff 48, the fluid 66 will naturally flow out of the outer cuff 48 and back into the syringe 64 or through the valve 67, thereby slowly deflating the outer cuff 48.

When deflating the outer cuff 48 by allowing the fluid 66 to flow back into the syringe 64, the outer cuff 48 will ideally deflate at a steady rate. To ensure a steady rate, the sliding friction between the syringe 64 and the plunger 70 must be low. If the sliding friction is too high, the fluid 66 will not naturally flow back into the syringe 64. To reduce the sliding friction, the syringe 64 is ideally a glass or plastic syringe with the plunger 70 made of rubber. In another potential embodiment, the syringe 64 is glass with a fitted tungsten or stainless steel plunger 70. Additionally, the plunger 70 may be coated with a fluoropolymer, silicone oil, mineral oil, or some other lubricant to reduce the sliding friction between the plunger 70 and the wall 72 of the syringe 64.

Referring to FIG. 16, as the outer cuff 48 is deflating, the pressure of the inner cuff 46 is continuously monitored using the manometer 62. The pressure of the inner cuff 46 will steadily drop as the outer cuff 48 deflates. Eventually the outer cuff 48 will begin to separate from the tracheal wall 68. As this separation begins, the outer cuff 48 will tend to resist separating from the tracheal wall 68 because the outer cuff 48 has adhered to the tracheal wall 68. However, as the outer cuff 48 continues to deflate, the elastic material of the outer cuff 48 will naturally tend to contract to its non-expanded form. Thus, the outer cuff 48 will eventually separate from the tracheal wall 68. At this separation point, the pressure of the inner cuff 46, as measured by the manometer 62, may increase suddenly due to the elastic material of the outer cuff 48 suddenly separating from the tracheal wall 68 and returning to its non-expanded state. This sudden contraction may cause a sudden decrease in the volume of the outer cuff 48 and a responsive increase in pressure of the inner cuff 46. Alternatively, rather than increasing suddenly, the pressure of the inner cuff 46 may remain constant for a short period of time at the separation point. While the rate of change in pressure of the outer cuff 48 and the inner cuff 46 remains relatively constant during the deflation of the outer cuff 48, the separation point represents a variance in the rate of change of the pressure of the fluid 66. After the separation point, the outer cuff 48 will resume deflating at a relatively constant rate, albeit at a slower rate than before the separation point due to the lower pressure of the fluid 66 after separation. The difference in the rate of change of pressure in the outer cuff 48 and the inner cuff 46 before and after the separation point provide an additional, measurable variance in the rate of change of the pressure of the fluid 66. Due to this variance, the separation point can be found and the pressure of the inner cuff 46 at the separation point is recorded. For increased accuracy, the outer cuff 48 can be inflated and then deflated multiple times to find the separation point and the corresponding pressure of the inner cuff 46. The separation point corresponds to the point at which the outer cuff 48 is applying zero pressure to the tracheal wall 68, but still contacting it.

Based on the separation point and the corresponding pressure of the inner cuff 46, the clinician is able to determine to what pressure to inflate the outer cuff 48. To achieve a seal between the tracheal wall 68 and the outer cuff 48, the outer cuff 48 should be inflated, at a minimum, to the point where the pressure of the inner cuff 46 equals the pressure of the inner cuff 46 at the separation point. However, to ensure that there is a proper seal the outer cuff 48 is ideally inflated to a point where the pressure of the inner cuff 46 is 5 to 50 cm $H_2O$ greater than the pressure at the separation point, although that range can be adjusted. To prevent patient discomfort and tracheal ischemia, the outer cuff 48 should not be inflated to a pressure much greater than the given range. Since clinicians do not know the tracheal diameter of any given patient, the separation point allows clinicians to accurately determine the pressure needed to create a proper seal for each individual patient. Therefore, this process lessens the risk of over pressurizing the inflatable cuff 42 and causing patient discomfort and ischemia. Additionally, this process ensures a proper seal without cuff folds between the inflatable cuff 42 and the tracheal wall 68.

For there to be a measurable separation point and a corresponding pressure jump or pressure pause in the inner cuff 46, the outer cuff 48 is ideally made of a material that adheres to the tracheal wall 68. As discussed in a previous embodiment and shown in FIG. 8, muco-adhesive materials can be used, either as part of the outer cuff 48 or as an additional layer on top of the outer cuff 48. The muco-adhesive layers or patterns can enhance the visibility of the separation point for clinicians performing this procedure.

In another embodiment, the outer cuff 48 can be made of a porous material such as the porous cuff 32 described in FIG. 9. Additionally, the fluid used to inflate the outer cuff 48 can be an aqueous-jelly solution of FIG. 9 that is designed to weep through the outer cuff 48 into the trachea 70. The aqueous-jelly solution can then act as an adhesive or bonding agent that helps ensure a proper seal between the tracheal wall 68 and the outer cuff 48.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A method of sealing a trachea, comprising:
    inserting a tracheal tube comprising an inflatable cuff into a trachea comprising a tracheal wall, the inflatable cuff comprising a compliant material;
    inflating the inflatable cuff with a fluid to a first pressure that exceeds a second pressure necessary to create a seal between the inflatable cuff and the tracheal wall;
    deflating the inflatable cuff by releasing the first pressure to allow the fluid to flow out of the inflatable cuff without applying vacuum pressure to the fluid;
    evaluating a rate of change of pressure of the fluid in the inflatable cuff while the inflatable cuff is deflating;
    identifying a variance in the rate of change of pressure corresponding to a third pressure at which the inflatable cuff at least partially separates from the tracheal wall;
    determining the second pressure by analyzing the third pressure; and
    reinflating the inflatable cuff to the second pressure.

2. The method of claim 1, wherein:
the second pressure is 0 to 50 centimeters of water more than the third pressure.

3. The method of claim 1, wherein:
the fluid in the inflatable cuff comprises a liquid.

4. The method of claim 3, wherein:
the fluid in the inflatable cuff further comprises a water soluble jelly.

5. The method of claim 1, further comprising:
repeating the steps of inflating the inflatable cuff and deflating the inflatable cuff, wherein the third pressure is determined by analyzing a number of identified variances of rates of change of pressure during the plurality of deflating steps.

6. The method of claim 1, wherein:
the compliant material of the inflatable cuff has a compliance of 20 to 500 percent.

7. The method of claim 1, wherein the compliant material of the inflatable cuff has a porosity of 0.00001% to 0.5%.

8. The method of claim 1, wherein:
the tracheal tube comprises an endotracheal tube.

9. The method of claim 1, wherein:
the tracheal tube comprises a tracheostomy tube.

10. The method of claim 1, wherein:
the pressure of the fluid in the inflatable cuff is measured using a manometer.

11. The method of claim 1, wherein:
the steps of inflating and deflating the inflatable cuff further comprises using a syringe filled with the fluid to inflate and deflate the inflatable cuff.

12. The method of claim 1, wherein:
the inflatable cuff is an outer cuff and the fluid is an outer cuff fluid, the tracheal tube further comprising an inner cuff, wherein the outer cuff surrounds the inner cuff; and
further comprising inflating the inner cuff with an inner cuff fluid after the step of inserting a tracheal tube;
wherein the step of evaluating a rate of change of pressure comprises measuring the rate of change of pressure of the inner cuff fluid while the outer inflatable cuff is deflating, the rate of change of pressure of the inner cuff fluid being responsive to the rate of change of pressure of the outer cuff fluid.

13. The method of claim 12, wherein:
the step of inflating the inner cuff with an inner cuff fluid further comprises fully inflating the inner cuff and then deflating the inner cuff so that the inner cuff is partially inflated.

14. The method of claim 12, wherein:
the inner cuff is comprised of a semi-compliant material, the semi-compliant material having a compliance of 5 to 30 percent.

15. The method of claim 12, wherein:
the second pressure is 0 to 50 centimeters of water more than the third pressure.

16. The method of claim 12, wherein:
the inner cuff fluid comprises a gas.
17. The method of claim 12, wherein:
the outer cuff fluid comprises a liquid.
18. The method of claim 1, wherein:
the second pressure is 0 to 50 centimeters of water more than the third pressure, the fluid in the inflatable cuff comprising a liquid, the compliant material having a compliance of 20 to 500 percent;
further comprising repeating the steps of inflating the inflatable cuff and deflating the inflatable cuff, wherein the third pressure is determined by analyzing a number of identified variances during the plurality of deflating steps;
wherein the steps of inflating and deflating the inflatable cuff comprises using a syringe filled with the fluid to inflate and deflate the inflatable cuff, the syringe having a plunger pressure less than the third pressure.
19. The method of claim 12, wherein:
the step of inflating the inner cuff with an inner cuff fluid further comprises fully inflating the inner cuff and then deflating the inner cuff so that the inner cuff is partially inflated; and
the inner cuff is comprised of a semi-compliant material, the semi-compliant material having a compliance of 5 to 30 percent, the inner cuff fluid comprises a gas, the outer cuff fluid comprises a liquid, and the second pressure is 0 to 50 centimeters of water more than the third pressure.

\* \* \* \* \*